United States Patent

Yamazaki et al.

[11] Patent Number: 5,593,586
[45] Date of Patent: Jan. 14, 1997

[54] GRANULOCYTE ADSORBING CARRIER AND GRANULOCYTE REMOVER

[75] Inventors: Kazutoshi Yamazaki, Ohtsu; Kazuo Shinmura, Osaka; Yoshiko Abe, Amagasaki, all of Japan

[73] Assignees: Sekisui Kagaku Kogyo Kabushiki Kaisha of Osaka, Japan, Osaka; Japan Immuno Research Lab. Co., Ltd. of Gunma, Japan, Takasaki, both of Japan

[21] Appl. No.: 407,601

[22] Filed: Mar. 21, 1995

Related U.S. Application Data

[62] Division of Ser. No. 222,710, Apr. 4, 1994, Pat. No. 5,525,279.

[51] Int. Cl.⁶ .................... B01D 24/00; B01D 39/04
[52] U.S. Cl. .................... 210/435; 210/483; 210/503
[58] Field of Search ................... 210/263, 287, 210/435, 483, 484, 488, 497.01, 502.1, 503; 422/101, 102

[56] References Cited

U.S. PATENT DOCUMENTS

| | | | |
|---|---|---|---|
| 4,256,588 | 3/1981 | Hoehn et al. | 210/692 |
| 4,701,267 | 10/1987 | Watanabe et al. | 210/335 |

FOREIGN PATENT DOCUMENTS 0319961  6/1989  European Pat. Off. .

*Primary Examiner*—John Kim
*Attorney, Agent, or Firm*—Armstrong, Westerman, Hattori, McLeland & Naughton

[57] ABSTRACT

Disclosed herein are a granulocyte adsorbing carrier which is provided on its surface with irregularities having a center line average height Ra of 0.2 to 10 μm and a mean spacing Sm of unevenness being within a range of 5 to 200 μm, and a granulocyte remover employing the granulocyte adsorbing carrier.

3 Claims, 6 Drawing Sheets

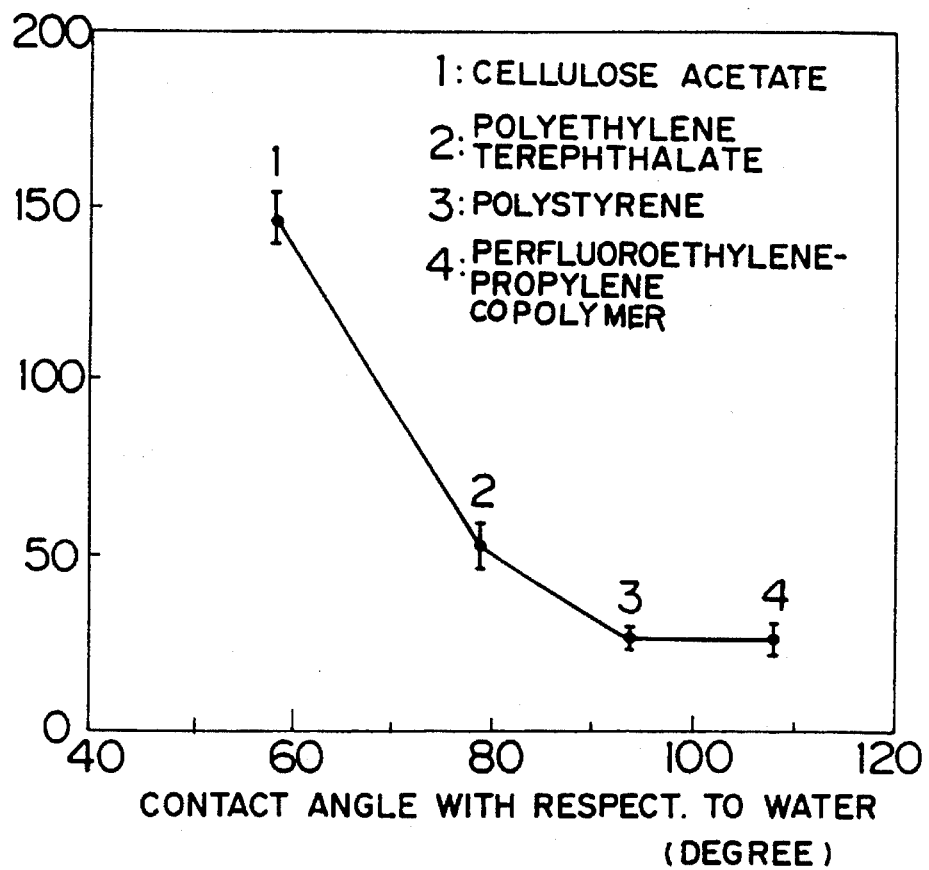
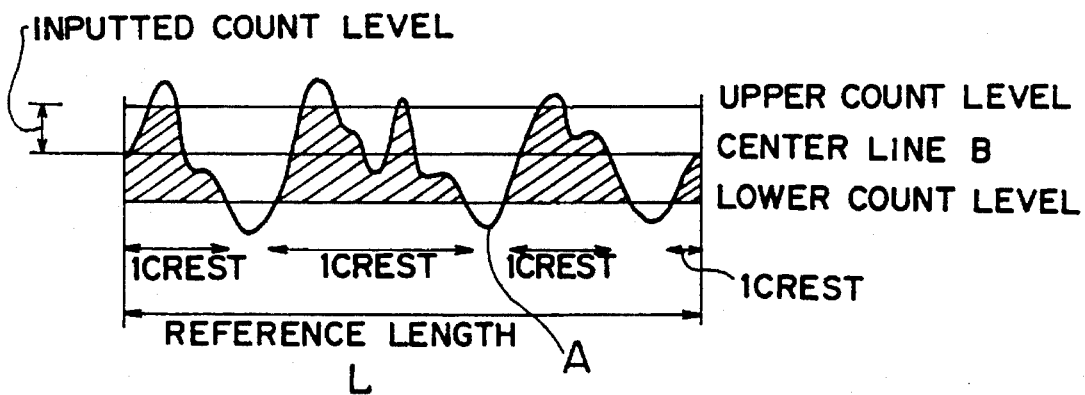

GRANULOCYTE ADSORBING CARRIER AND GRANULOCYTE REMOVER

This is a division, of application Ser. No. 08/222,710 filed Apr. 4, 1994, now U.S. Pat. No. 5,525,279.

BACKGROUND OF THE INVENTION

1. Field of the Invention

The present invention relates to a granulocyte adsorbing carrier for selectively removing granulocytes from blood and a granulocyte remover employing the granulocyte adsorbing carrier.

2. Description of the Background Art

In relation to a method of separating granulocytes from blood, there have generally been proposed a centrifugal separation method utilizing difference in specific gravity, and a method utilizing a material such as cotton, nylon fiber, polyester fiber or silicone-treated glass wool, for example, for allowing selective adhesion of granulocytes (Japanese Patent Laying-Open Nos. 54-46812 (1979) and 57-11920 (1982), for example).

In the method utilizing difference in specific gravity, however, much labor and a long-time operation are required for separating the granulocytes, while lymphocytes are easy to contaminate. As compared with this method, the method utilizing a material for allowing selective adhesion of granulocytes can conceivably efficiently adsorb the granulocytes in a simple operation. In such a method of selectively adsorbing granulocytes, the surface area of an adsorbent is generally maximized thereby improving adsorbability. Therefore, the adsorbent is mainly prepared from fiber.

However, it is impossible to further selectively adsorb the granulocytes by merely increasing the adsorption area of the adsorbent. In fact, Japanese Patent Publication No. 58-54126 (1983) describes that not only granulocytes but lymphocytes are adsorbed.

As disclosed in Japanese Patent Laying-Open No. 2-193069 (1990), on the other hand, the G-L ratio of a granulocyte number G to a lymphocyte number L in a cancer patient is a host marker, which can conceivably serve as effective means for judging a pathologic change of the patient in clinical treatment. It is also suggested that preferable influence is exerted on cancer treatment when the G-L ratio is reduced by selectively removing granulocytes from the blood of the patient.

The aforementioned Japanese Patent Laying-Open No. 2-193069 (1990) discloses a carrier such as polystyrene, cellulose acetate, nylon, polytrifluoroethylene or polyethylene terephthalate having higher affinity to granulocytes as compared with lymphocytes as a granulocyte adsorbing carrier which can be applied to the aforementioned judgement of a pathologic change of a cancer patient or cancer treatment, and describes that granulocytes can be selectively adsorbed by such a carrier. For the purpose of the aforementioned cancer treatment, however, awaited are a carrier and a granulocyte remover which can further selectively adsorb granulocytes.

While Japanese Patent Laying-Open No. 2-193069 (1990) illustrates polystyrene, cellulose acetate, 6-nylon and polyethylene terephthalate as exemplary samples for forming the granulocyte adsorbing carrier as hereinabove described, this gazette further clarifies that the cellulose acetate exhibits excellent granulocyte adsorbability in particular.

However, it is impossible to mold cellulose acetate without employing a plasticizer. Therefore, the cellulose acetate is generally mixed with a plasticizer, to be molded. The plasticizer which can be employed for the cellulose acetate is prepared from an adipic acid, citric acid, glycerolic, phosphoric acid, phthalic acid, sebacic acid or succinic acid plasticizer.

When the aforementioned plasticizer is mixed with the cellulose acetate for molding the same, however, a problem of toxicity arises since the plasticizer component flows out from the adsorbing carrier as obtained into the blood. Further, dioctyl phthalate, being a generally employed plasticizer which is approved for a medical device such as a blood circuit, cannot be applied to cellulose acetate.

While it is obviously preferable to employ a cellulose acetate carrier as a granulocyte adsorbing carrier for a granulocyte remover which is employed for extracorporeal circulation, there has been provided no granulocyte adsorbing carrier of cellulose acetate containing a plasticizer in an approvable amount.

SUMMARY OF THE INVENTION

The present invention has been proposed in order to satisfy the aforementioned requirement, and an object thereof is to provide a granulocyte adsorbing carrier which can further effectively remove granulocytes selectively from blood.

Another object of the present invention is to provide a granulocyte remover which can further effectively remove granulocyte selectively from blood.

Still another object of the present invention is to provide a method which can prepare a cellulose acetate granulocyte adsorbing carrier having excellent granulocyte adsorbability, which is excellent in safety with an extremely small content of a plasticizer.

According to a wide aspect of the present invention, provided is a granulocyte adsorbing carrier which is provided on its surface with irregularities having a center line average height Ra of 0.2 to 10 μm and a mean spacing Sm of unevenness of 5 to 200 μm.

The inventive granulocyte adsorbing carrier can effectively and selectively adsorb granulocytes due to the irregularities provided on its surface. This is conceivably because adsorbability for the granulocytes which are adhesive cells is varied with the irregularities provided on the surface while that for the lymphocytes which are nonadhesive cells is not much dependent on the surface roughness and hence adsorbability for the granulocytes is extremely improved by the irregularities within the aforementioned specific ranges.

Thus, it is possible to selectively and efficiently remove granulocytes from blood by applying the granulocyte adsorbing carrier and the granulocyte remover according to the present invention to cancer treatment by extracorporeal circulation etc. Therefore, it is possible to correct an abnormally high G-L ration of a cancer patient for approximating the same to a normal value by employing the granulocyte adsorbing carrier and the granulocyte remover according to the present invention.

The granulocyte adsorbing carrier and the granulocyte remover according to the present invention are applicable not only to extracorporeal circulation but to removal of granulocytes from collected blood or facilitation of reduction in granulocyte concentration.

According to a specific aspect of the present invention, provided is a granulocyte remover which comprises a granulocyte adsorbing part storing the aforementioned granulocyte adsorbing carrier, a blood incurrent part for introducing blood into the granulocyte adsorbing part, and a blood excurrent part for discharging the blood from the granulocyte adsorbing part to the exterior.

According to the inventive granulocyte remover, the granulocyte adsorbing part is formed by the granulocyte adsorbing carrier which is provided on its surface with irregularities within the aforementioned specific ranges, whereby it is possible to selectively and efficiently separate/remove the granulocytes from blood.

According to still another aspect of the present invention, provided is a method of preparing a cellulose acetate granulocyte adsorbing carrier containing not more than 1.2 percent by weight of a plasticizer by molding cellulose acetate with a plasticizer of acetyltriethyl citrate and extracting the plasticizer with methanol.

The granulocyte adsorbing carrier obtained by the inventive method is made of cellulose acetate, which is particularly excellent in granulocyte adsorbability. According to the present invention, the cellulose acetate, which cannot be independently subjected to injection molding or extrusion molding, is molded with a plasticizer of acetyltriethyl citrate (hereinafter referred to as ATEC).

According to the present invention, a plasticizer of ATEC is employed to mold cellulose acetate which is excellent in granulocyte adsorbability and the ATEC is extracted by methanol after the molding, whereby it is possible to obtain a granulocyte adsorbing carrier having high safety with an ATEC content of not more than 1.2 percent by weight. When the granulocyte adsorbing carrier obtained by the present invention is applied to treatment of a cancer patient with extracorporeal circulation, therefore, it is possible to reduce his G-L ratio without exerting a bad influence on him.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2 illustrates relations between various films having different contact angles and leukocyte adsorbability levels;

FIG. 3 is a diagram for illustrating a method of defining crests for obtaining a mean spacing Sm of unevenness;

DESCRIPTION OF THE PREFERRED EMBODIMENTS

Figure 1:
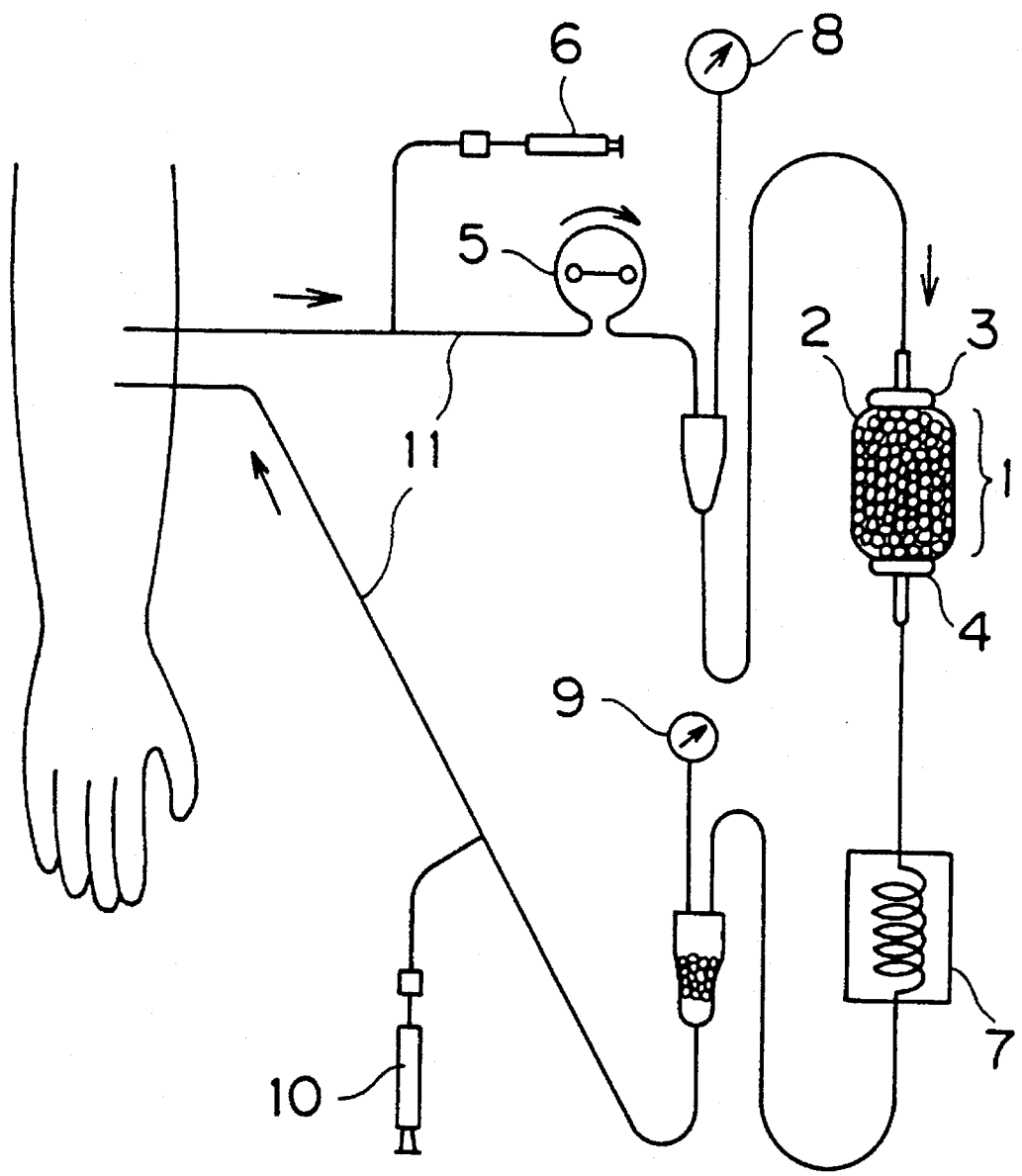
FIG. 1 is a schematic block diagram for illustrating exemplary application of a granulocyte remover according to the present invention.

A granulocyte adsorbing carrier and a granulocyte remover according to the present invention are now described in detail, followed by detailed description of a method of preparing the granulocyte adsorbing carrier according to the present invention.

A. Detailed Description of Granulocyte Adsorbing Carrier and Granulocyte Remover
(Progress of the Invention)

In order to attain further selective adsorption of granulocytes, the inventors have noted difference of characteristics between lymphocytes and granulocytes. They have considered that not only increase in contact area but surface shapes, i.e., surface states of portions coming into contact with the granulocytes extremely exert on adsorption of the granulocytes since the granulocytes which are called phagocytes or adherent cells have specific reaction with respect to foreign materials.

As to adsorbability levels of various materials for neutrophilic leukocytes mainly composing granulocytes, it has been reported that neutrophilic leukocytes extremely adhere to materials having contact angles of about 70° with respect to water (Summary of Lectures in 19-th Biomedical Polymer Symposium in Japan, THE SOCIETY OF POLYMER SCIENCE, JAPAN, Jun. 11, 1990, pp. 51 to 52).

The inventors have employed four types of films having different angles within a range of about 60 to 110°, including a cellulose acetate film (hereinafter referred to as a CA film), a polyethylene terephthalate film (hereinafter referred to as a PET film), a polystyrene film (hereinafter referred to as a PSt film), and a perfluoroethylene-propylene copolymer film (hereinafter referred to as an FEP film), to measure amounts of leukocytes adhering to the films along film adsorption test described later. Consequently, they have obtained results which were similar to those reported in the aforementioned literature, as shown in FIG. 2. In other words, the amounts of adsorbed leukocytes were reduced as the contact angles were increased from about 70°.

On the other hand, the inventors have also made another adsorption test on CA, PET and FEP films which were polished in various roughness values in parallel with the aforementioned adsorption test, to find that these films adsorbed extremely larger amounts of leukocytes as compared with unpolished films having smooth surfaces.

Namely, they have found that the aforementioned three types of films exhibited leukocyte adsorbability levels of about 4 to 11 times those of corresponding ones of unpolished films when these films were polished with sand paper of not more than 1200 meshes in roughness to have Ra values (described later) of at least 0.2 μm. It is to be noted that they have found that the FEP film, which had hardly adsorbed leukocytes in a smooth state, exhibited adsorbability similarly to the CA and PET films due to the polishing, regardless of the contact angle. This means that increase in leukocyte adsorbability of a material having proper surface roughness depends on not only increase in surface area but on surface irregularity, which facilitates adsorption of leukocytes. This is also backed up with the fact that the respective films polished with sand paper of 1200 meshes to be increased in leukocyte adsorbability exhibited Ra values of 0.6 to 0.7 μm, which were extremely small as compared with sizes of the leukocytes, and hence the contact areas were conceivably not much increased in these polished films.

The inventors have further found that the film must be provided with irregularities having an Ra value within a range of 0.2 to 10 μm as described later and a mean spacing Sm of unevenness within a range of 5 to 200 μm, to provide the present invention.

The term "Ra value" indicates the center line average height under JIS B0601-1982 and expresses the surface roughness, or heights of irregularities, of the material, and is a value that is obtained from the following formula, extracting a part of measuring length, 1, in the direction of its center-line from the roughness curve, y=f(x), and taking the center-line of this extracted part as x-axis and the direction of vertical magnification as y-axis:

$$R_a = \frac{1}{l} \int_0^1 |f(x)| dx.$$

The mean spacing Sm of unevenness is defined as follows:
(Mean Spacing Sm of Unevenness)

Under the present Japanese Industrial Standards, no standard is defined as to information on a surface direction of surface roughness although a standard is defined as to information on a height direction. According to the present invention, however, the irregularities are limited also by spacings between the irregularities in a surface direction, as clearly understood from Examples described later. According to the present invention, therefore, the mean spacing Sm of unevenness is employed to define the range of the irregularities in the surface direction.

The mean spacing Sm of unevenness is obtained as follows:

First, upper and lower count levels are drawn with respect to a center line B of a roughness curve A shown in FIG. 3 at positions of constant heights and depths respectively. When the upper count level intersects with the roughness curve A in at least one point between two points where the lower count level intersects with the roughness curve A, a "crest" is defined.

Figure 4:
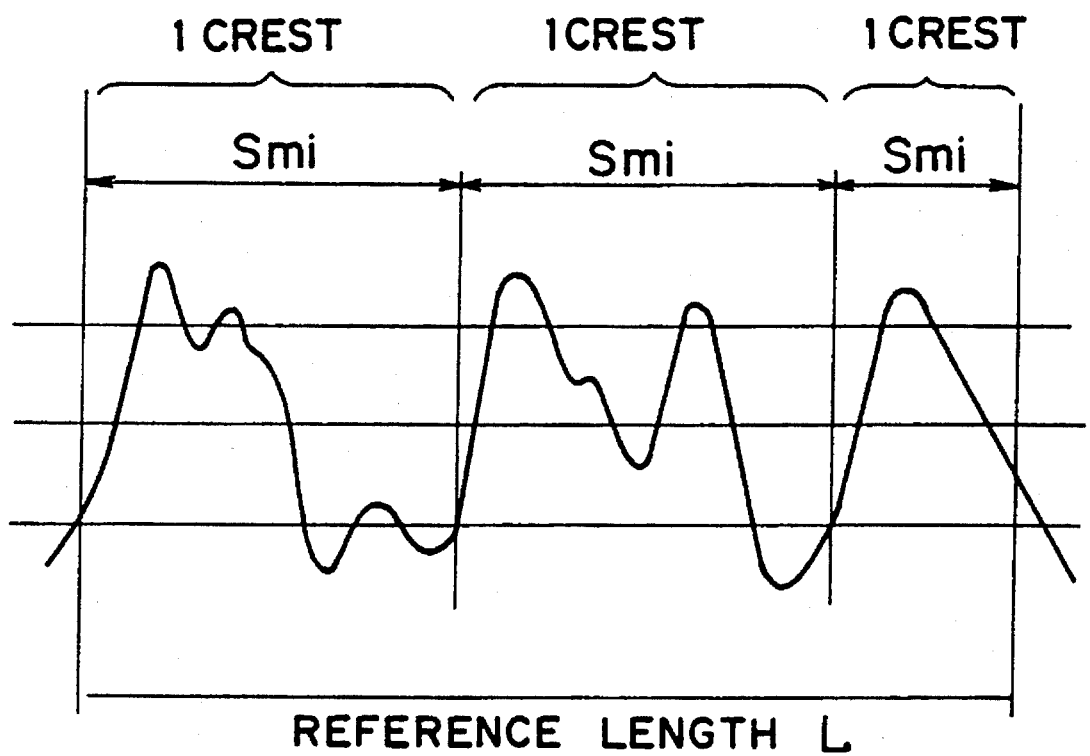
FIG. 4 is a diagram for illustrating a method for obtaining the mean spacing Sm of unevenness.

Assuming that Smi represents a spacing between crests which are present in a reference length L as shown in FIG. 4, the mean spacing Sm of unevenness is defined as follows:

$$Sm = \frac{1}{n} \sum_{i=1}^{n} Smi$$
(n: Number of Crests)

Namely, the mean spacing Sm unevenness indicates a mean value of spacings between crests which are present in the reference length. Thus, the condition of irregularities in a surface direction is defined by the mean spacing Sm of unevenness.
(Granulocyte Adsorbing Carrier)

The inventors have polished PET films having the aforementioned Ra values of at least 0.2 μm with sand paper of 1200 meshes in various polishing times to prepare films having Sm values of 474, 374, 213, 101, 56 and 31 μm respectively and carried out a film adsorption test as described later, to find that the total amounts of adsorbed leukocytes were abruptly increased when the Sm values were not more than 200 μm. Thus, the film must have a center line average height of at least 0.2 μm, and a mean spacing Sm of unevenness of not more than 200 μm.

In the aforementioned film adsorption test, however, it is difficult to judge whether the leukocytes are granulocytes or lymphocytes, although adsorbability for the total number of the leukocytes can be confirmed. Therefore, the inventors have made a bead adsorption test as described later, in order to confirm whether or not the total number of the leukocytes was changed by granulocytes. Consequently, they have found that granulocyte adsorbability was extremely improved in beads having surface roughness in the inventive range as compared with unpolished beads, while adsorbability substantially remained unchanged with respect to lymphocytes. Thus, it is conceived that the granulocytes which were adherent cells were further effectively adsorbed by or adhered to the carrier due to adhesion thereof while adsorbability for the lymphocytes which are nonadherent cells remained substantially unchanged after polishing since the surface are was hardly increased in the adsorbing carrier having surface roughness within the inventive range. Consequently, it is conceivably possible to selectively adsorb the granulocytes by employing the inventive adsorbing carrier.

The carrier employable in the present invention can be prepared from any material so far as the same is not deleterious to the human body with no elution of an additive such as a harmful metal or a plasticizer in extracorporeal circulation, for example. In other words, it is possible to employ a synthetic or natural organic polymer material, or an inorganic material such as glass or alumina, which is provided on its surface with irregularities of 0.2 to 10 μm in center line average height and 5 to 200 μm in mean spacing Sm of unevenness. Examples of synthetic and natural organic polymer materials are cellulose acetate, polystyrene, nylon, polytetrafluoroethylene, polytrifluoroethylene, perfluoroethylene-propylene copolymer, polyethylene terephthalate, polyethylene, polyvinyl chloride, acrylic resin, ethyl cellulose and the like.

The granulocyte adsorbing carrier may have arbitrary shape and size and it is possible to use the material in any shape such as that in the form of a film, fiber or beads, while a carrier which is in the form of beads in preferable in consideration of easiness in charging in an extracorporeal circulation column and polishing. A carrier in the form of beads can be prepared by obtaining spherical bodies by a general method such as injection molding or suspension polymerization. While the beads are not particularly restricted in particle diameter, the same may generally be about 0.1 to 10 mm in diameter for increasing contact areas, for example, and more preferably 0.2 to 5 mm in diameter.

On the other hand, surface roughness is generally provided by polishing, while it is also possible to prepare a carrier having the aforementioned specific surface roughness by another method. For example, it is possible to physically or chemically fix particulates onto the surface of the carrier, or to employ a carrier having a porous surface.

The method of fixing fine particulates onto the carrier surface is carried out by coating particulates of 0.1 to 20 μm, for example, thereby effectively adsorbing granulocytes. The particulates employed in this method can be prepared by emulsion-polymerizing or suspension-polymerizing an independent vinyl monomer such as a styrene monomer or an acrylate monomer, or a mixture of at least two such components. These particulates are preferably prepared from a copolymer with a polyfunctional monomer such as divinyl benzene, for example, having at least two functional groups.

A method of coating such particulates is now described. First, these particulates are suspended in a solution in which about 0.1 to 5 percent by weight of a synthetic or natural polymer is dissolved for serving as a binder for coating. Then, a previously molded carrier of an organic or inorganic material in the form of beads, fiber or a film is dipped in this suspension and thereafter dried, to prepare the inventive granulocyte adsorbing carrier. In this case, the Ra and Sm values can be adjusted by the sizes of the particulates and the concentration of the suspended particles respectively.

A porous carrier may also be in the form of a film, fiber or beads, and only its surface or the overall carrier may have porosity. A carrier having a porous surface can be obtained by spraying a solution, which is prepared by dissolving about 0.1 to 5 percent by weight of a synthetic or natural polymer in a good solvent therefor as a coating solution, to a carrier of an organic or inorganic material in the form of beads, fiber or a film and heating/drying the same. On the other hand, an entirely porous adsorbing carrier can be prepared by a general method of preparing a porous film or porous beads. For example, it is possible to prepare a porous film by dissolving a synthetic polymer in a good solvent and spreading the same on a glass plate for forming a casting film, and thereafter washing the film with a poor solvent for the synthetic polymer and extracting the good solvent.

In the porous carrier, adjustment of Ra and Sm values is attained by adjusting the diameters and the amount of the pores, which can be easily adjusted by changing the type and the amount of the solvent for dissolving the carrier.

(Granulocyte Remover)

The granulocyte remover according to the present invention is now described. The inventive granulocyte remover has such a structure that a blood incurrent part and a blood excurrent part are connected to a granulocyte adsorbing part storing the aforementioned granulocyte adsorbing carrier in accordance with claim 1. An exemplary structure of the granulocyte remover is now described with reference to FIG. 1. Referring to FIG. 1, numeral 1 denotes a granulocyte adsorbing part, which is filled up with a granulocyte adsorbing carrier 2 having surface roughness Ra of 0.2 to 10 μm and a mean spacing Sm of unevenness of 5 to 200 μm. A blood incurrent part 3 is connected to an end of the granulocyte adsorbing part 1 for introducing target blood (blood of a patient having a high G-L ratio), while a blood excurrent part 4 is connected to another end for discharging the blood, which is introduced into the granulocyte adsorbing part 1 so that granulocyte are adsorbed/removed by contact with the adsorbing carrier 2, to the exterior of the granulocyte adsorbing part 1. The blood incurrent and excurrent parts 3 and 4 may be provided with filters, in order to prevent the carrier 2 from flowing out.

The granulocyte adsorbing part 1 can be formed by a substantially cylindrical column, as shown in FIG. 1. While this column can be made of synthetic resin such as polycarbonate or glass, for example, the material for this column is not particularly restricted. The column forming the adsorbing part 1 is provided with an inlet and an outlet in its upper and lower ends for forming the blood incurrent part 3 and the blood excurrent part 4 respectively, as shown in FIG. 1.

The granulocyte remover according to the present invention, which can be so employed as to continuously remove granulocytes by extracorporeal circulation in accordance with ordinary plasmapheresis for improving the G-L ratio, can comprise a piping 11 and a blood pump 5 of innocuous materials such as silicon rubber tubes or polyvinyl chloride, for example, for serving as transportation materials.

The circuit for circulating the blood which is transmitted from the blood excurrent part 4 may be provided with an arteriomanometer 8 and a phlebomanometer 9 for confirming normal blood circulation, a drug inlet 6 for administering a drug such as heparin, for example, for preventing the blood from coagulation, another drug inlet 10 for injecting a drug such as protamine, for example, for preventing action of an anticoagulant, and a heater 7 for increasing the temperature of the blood which is lowered during extracorporeal circulation. It is also possible to provide an ordinary detector for detecting a hemogram of the circulating blood and a blood component supplier for making up for deficit of blood components other than the granulocytes caused by the present invention.

B. Detailed Description of Method of Preparing Granulocyte Adsorbing Carrier

In general, a plasticizer has strong toxicity and hence it is necessary to minimize the final concentration of the plasticizer contained in the molding. In the inventive method of preparing a granulocyte adsorbing carrier, therefore, ATEC is employed as the plasticizer and extracted after molding, so that the ATEC content is reduced.

The aforementioned ATEC is certificated by the FDA, the USA, as a plasticizer for a medical synthetic resin product. Approval of a medical device for an extracorporeal circulation circuit system or the like is generally referred to the Notification of Director-general of Pharmaceutical affairs bureau M.H.W. No. 494 dialysis type artificial kidney approval standards. Such a device must conform to an eluate test of a dialyzer. Further, a circulating solution preferably conforms to an insoluble particulate test of an "injection" under General Rules for Preparations, the Pharmacopeia of Japan, 11th Edition.

Referring to the aforementioned standards, diethyl phthalate which is generally employed as a plasticizer is not conformable to an ultraviolet ray absorption test of an eluate, due to remarkable ultraviolet ray absorption. On the other hand, ATEC is optimum as a plasticizer for a medical device forming an extracorporeal circulation circuit since the same has rather small ultraviolet ray absorption and satisfies the aforementioned standards.

According to the present invention, ATEC is utilized as the plasticizer and extracted with methanol after molding, so that the ATEC content is reduced to not more than 1.2 percent by weight. The ATEC is extracted with methanol for the following reason:

The plasticizer can be extracted through a solvent allowing no dissolution of cellulose acetate, which is the basic component of the granulocyte adsorbing carrier, but dissolving the plasticizer, by a reflux method or a batch method. However, it is necessary to take extraction efficiency and safety into consideration in selection of the extraction solvent. Methanol or ethanol having strong polarity is preferable in consideration of the extraction efficiency. However, ethanol exerts such influence on cellulose acetate resin that beads are whitened when a cellulose acetate carrier is prepared in the form of beads and the carrier cannot pass an insoluble particulate test of the "injection" under General Rules for Preparations, the Pharmacopeia of Japan, 11th Edition, through a particulate generation test employing the beads.

On the other hand, a solvent exerting no influence on cellulose acetate resin can be prepared from isopropyl alcohol, n-hexane or diethyl ether having relatively high hydrophobicity. However, this solvent is inferior in extraction efficiency.

According to the present invention, therefore, methanol is employed as a solvent for extracting ATEC for the aforementioned reason. The method of extracting ATEC with methanol is not restricted in particular, while batch system extraction is preferably employed in order to industrially extract ATEC. The extraction temperature is properly set at a level of 40° to 50° C., for example, which is slightly lower than the boiling point of methanol. While ATEC can be extracted at a low temperature, it is necessary to increase the extraction time. The extraction time is properly selected in a range of at least 30 minutes and not more than 2 hours, since it takes for overall beads about 30 minutes to be imbibed in ethanol in cellulose acetate resin in the form of beads of 2.3 mm in diameter at 50° C. while extraction efficiency is deteriorated due to increase in ATEC concentration in methanol if the extraction time is too long.

As to the amount of methanol which is employed with respect to the cellulose acetate resin in extraction, it is preferable to use the methanol in a volume of at least twice that of the cellulose acetate resin in the form of beads, so that the beads are completely dipped in the methanol. As to the number of times of extraction which is varied with the shape and the particle diameter of the cellulose acetate resin, it is possible to reduce the content of the plasticizer to not more than 1.2 percent by weight through extraction of 4 to 5 times if the beads forming the cellulose acetate resin are 2.3 mm in diameter.

It is conceivably difficult to industrially reduce the ATEC content to not more than 0.1 percent by weight in practice, since about 0.1 percent by weight of ATEC still remains also when the aforementioned cellulose acetate resin in the form of beads is subjected to Soxhlet extraction for 48 hours.

Comparing the aforementioned ATEC with dioctyl phthalate, which is a typical plasticizer approved for a medical device, as to toxicity, the former has toxicity of four times that of the latter in lethal dosage of intravenous administration. When a plasticizer of ATEC was extracted through methanol from cellulose acetate resin which was molded with the plasticizer so that the residual ATEC concentration was not more than 1.2 percent by weight and this cellulose acetate resin was filled up in a column for circulating blood plasma, however, it was confirmed that the amount of ATEM eluted in the blood plasma was not more than 1/50 of that of dioctyl phthalate which was eluted in blood plasma when the blood plasma was circulated in a blood circuit for an artificial kidney.

Thus, it is understood possible to reduce elution toxicity of ATEC below that of dioctyl phthalate in a blood circuit for an artificial kidney by extracting ATEC from cellulose acetate resin which is molded with a plasticizer of the ATEC according to the inventive method through methanol.

When the plasticizer is thus prepared from ATEC, on the other hand, it is necessary to consider the amount of consumption of potassium permanganate in an elution test under the Notification of Director-general of Pharmaceutical affairs bureau M.H.W. No. 494 dialysis type artificial kidney device approval standards. When beads of 2.3 mm in diameter containing 30 percent by weight of ATEC obtained by injection molding were employed to carry out the aforementioned elution test in various numbers of times of batch extraction of methanol with residual ATEC contents of 4,3, 1.7 and 0.5 percent by weight respectively, it was recognized that the reference value of not more than 1 ml of consumption of potassium permanganate corresponds to a plasticizer content of not more than 1.2 percent by weight.

Thus, the lower limit of ATEC is 0.1 percent by weight, which is in an industrially extractable range, while the upper limit is not more than 1.2 percent by weight from the reference of consumption of potassium permanganate in the elution test.

According to the present invention, cellulose acetate is molded with the plasticizer of the aforementioned ATEC, while the molding method is not restricted in particular but is properly selected in response to the shape and the size of the granulocyte adsorbing carrier. In order to mold the cellulose acetate with ATEC, 20 to 50 parts by weight of the ATEC may be blended with 100 parts by weight of the cellulose acetate. It is difficult to mold the cellulose acetate if the amount of blending of the ATEC is less than 20 parts by weight. If the amount of blending of the ATEC exceeds 50 parts by weight, on the other hand, this amount is excessive for the molding and it takes time to finally reduce the ATEC content to not more than 1.2 percent by weight in extraction with methanol.

The granulocyte adsorbing carrier obtained by the inventive method is not particularly restricted in shape and size, but can be in an arbitrary shape other than the aforementioned cellulose acetate resin in the form of beads. In general, however, the granulocyte absorbing carrier preferably has a size which can be distinguished from blood cells, and a shape provided with a large contact area with the blood. In general, therefore, the granulocyte adsorbing carrier is provided in the form of beads having diameters of about 0.1 to 10 mm. In particular, the granulocyte adsorbing carrier obtained according to the present invention is preferably in the form of beads having diameters of 0.5 to 7 mm. When a granulocyte adsorbing part, i.e., a column, storing the granulocyte adsorbing carrier in the form of beads is employed, a high pressure is required for transporting the blood if the beads are too small in particle diameter, to cause coagulation, formation of thrombus, blinding with the thrombus, and reduction of the flow rate. Thus, the beads forming the granulocyte adsorbing carrier are preferably at least 0.5 mm in particle diameter, as hereinabove described. When the beads forming the granulocyte adsorbing carrier exceed 7 mm in particle diameter, on the other hand, granulocyte adsorbing efficiency is reduced due to reduction in surface area per unit volume.

While the granulocyte adsorbing carrier in the form of beads can be prepared by molding cellulose acetate with the aforementioned ATEC serving as a plasticizer through a molding method such as injection molding or extrusion molding, the particle diameters of the beads may be regularized by polishing after molding, if necessary.

EXAMPLES

Nonrestrictive Examples of the present invention and comparative examples are now described to clarify the present invention.

A. Examples of the Invention on Granulocyte Adsorbing Carrier and Granulocyte Remover First, description is made on methods of preparing and testing samples employed for Examples 1 to 16 and comparative examples 1 to 16 which are described later.

(1) Method of Forming Polished Film (Examples 1 to 12 and Comparative Examples 2, 3, 5, 6, 8, 9, 11 and 12)

Surfaces of films for serving as granulocyte adsorbing carriers were washed with methyl alcohol, and polished films having various surface roughness values were formed using an automatic polishing machine (PLANOPOL PEDEMAX (trade name)) by STRUERS CO., LTD. (Denmark) with sand papers of 220, 500, 1200, 2400 and 4000 meshes respectively.

(2) Film Adsorption Test (Examples 1 to 12 and Comparative Examples 1 to 12)

Figure 5A:
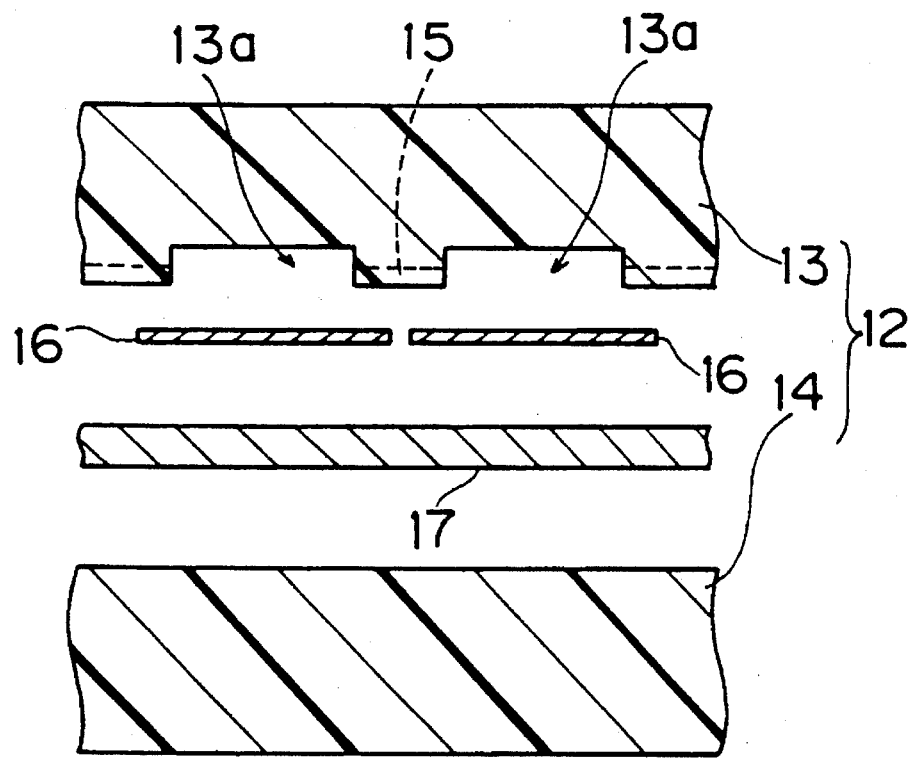
FIGS. 5A and 5B are sectional views for illustrating a film adsorption test respectively.
Figure 5B:
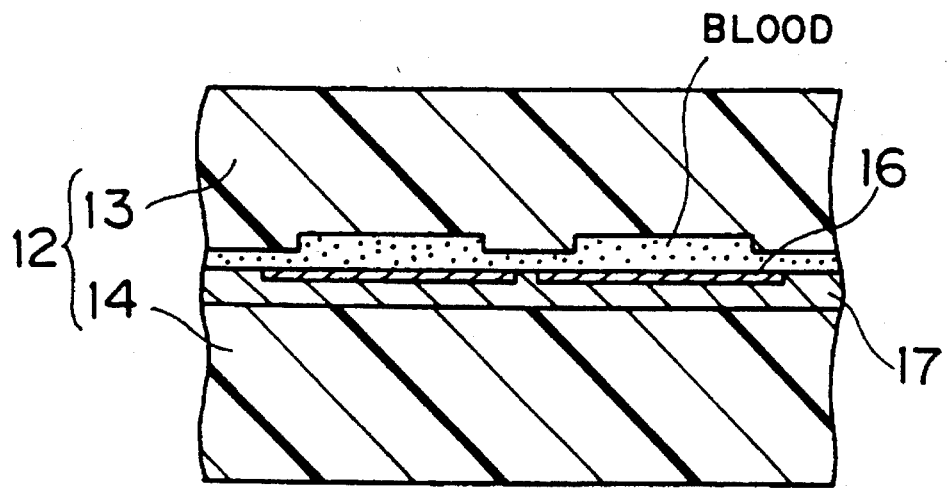

A testing set 12 of polycarbonate resin shown in FIGS. 5A and 5B was employed. This testing set 12 comprises upper and lower plates 13 and 14. The upper plate 13 is formed by a rectangular polycarbonate resin plate of 10 mm in thickness, 70 mm in width and 220 mm in length, and provided in its lower surface with a plurality of circular openings 13a of 10 mm in diameter and 2 mm in depth. These openings 13a are connected with each other by grooves 15 of 1 mm in depth and 2 mm in width.

Films 16 of each sample were cut into 20 by 20 mm square, washed with methyl alcohol and arranged under the lower surfaces of the openings 13a of the upper plate 13.

Then, the films 16 were brought into contact with the openings 13a, and the lower plate 14 of polycarbonate resin having a thickness of 10 mm was brought into pressure contact with and fixed to the same through a sheet member 17 of silicone rubber having a thickness of 2 mm. Then, an isotonic phosphoric acid buffer solution (pH=7.2: hereinafter referred to as PBS) was introduced into cells defined by the openings 13a of the testing set 12 at a flow rate 1 ml/min. for 10 minutes and thereafter replaced by 8 ml of heparinized normal blood and circulated at a flow rate of 1 ml/min. with a peristaltic pump, to make an adsorption test in a water bath at 37° C. for 1 hour.

Thereafter the films 16 were taken out from the testing set 12, washed with PBS similarly to the above, thereafter alcohol-fixed and subjected to May-Giemsa staining to prepare smear sample films, thereby obtaining numbers of leukocytes which were absorbed by the films per unit area by microscopic observation.

(3) Method of Measuring Surface Roughness

Center line average heights Ra (cutoff values: 0.8 mm in film and 0.08 mm in beads) and mean spacings Sm of unevenness described in relation to Examples and comparative examples were measured by a surface roughness tester (SURFCORDER SE-30D: trade name) by Kosaka Laboratory Ltd.

(4) Bead Absorption Experiment (Examples 13 and 14 and Comparative Examples 13 and 14)

Granulocyte adsorbing carriers were prepared from beads, to be subjected to granulocyte adsorption experiments as follows: First, the beads were dipped in a 300 ml of a 5 wt. % aqueous solution of a surface active agent (SCAT 20X-N (trade name)) by Dai-ichi Kogyo Seiyaku Co., Ltd. for 30 minutes. Then, the beads were washed with demineralized water five times, further washed with methanol twice and thereafter air-dried. Further, 3 g of the beads were introduced into a syringe of 5 ml in capacity and shaken/mixed at 37° C. for 1 hour with addition of 2 ml of heparinized normal blood, so that the blood components were adsorbed by the beads. 2 ml of blood was similarly added to a 5 ml syringe and also shaken/mixed at 37° for 1 hour, to prepare a control.

The blood as shaken/mixed was collected from the syringe to prepare smear samples, which were subjected to measurement of granulocytes and lymphocytes. The total number of leukocytes was measured by an automatic hemocyte analyzer Sysmex E-4000 (trade name) by TOA MEDICAL ELECTRONIC CORPORATION LIMITED. The number of adsorbed granulocytes was obtained from the total number of leukocytes, the granulocytes and the lymphocytes.

Examples 1 to 3 and Comparative Examples 1 to 3

FEP films (perfluoroethylene-propylene copolymer films of NEOFLON (trade mark) (registered trade mark) by Daikin Industries, Ltd.) were employed to form films which were polished in five stages in accordance with the aforementioned method of forming polished films. Values Ra and Sm were obtained as to an unpolished film and the films polished in five stages, which were then subjected to the aforementioned film adsorption test (2). Table 1 shows the results.

TABLE 1

Amount of Leukocytes Adsorbed FEP Film

| | Film | | | | | |
|---|---|---|---|---|---|---|
| | Comparative Example | | | Example | | |
| | 1 | 2 | 3 | 1 | 2 | 3 |
| | | | Polished | | | Polished |
| Item | Un-polished | 4000 meshes | 2400 | 1200 | 500 meshes | 220 |
| Ra Value (μm) | 0.05 | 0.09 | 0.41 | 0.71 | 1.67 | 2.94 |
| Sm Value (μm) | 246 | 79 | 96.5 | 20.4 | 51.5 | 68.7 |
| Amount of Adsorbed Leukocytes (pieces/mm$^2$) | 92 | 250 | 203 | 821 | 747 | 847 |
| Relative Adsorption Ratio | 1 | 2.72 | 2.21 | 8.92 | 8.12 | 9.21 |

As clearly understood from Table 1, the numbers of adsorbed leukocytes were abruptly increased when the Ra values exceeded 0.71 μm. In the film according to Example 1, for example, the number of adsorbed leukocytes reached 8.92 times that of the unpolished film (comparative example 1).

Further, the polished films according to Examples 2 and 3 having Ra values of 1.67 μm and 2.94 μm respectively exhibited high leukocyte adsorbability levels with amounts of adsorbed leukocytes of 8.12 times and 9.21 times as compared with that of the unpolished film.

On the other hand, the polished films (comparative examples 2 and 3 and Examples 1 to 3) exhibited Sm values in a range of 20 to 100 μm, while the unpolished film exhibited a value of 246 μm.

Examples 4 to 6 and Comparative Examples 4 to 6

Films of Examples 4 to 6 and comparative examples 4 to 6 were prepared similarly to Examples 1 to 3 and comparative examples 1 to 3, except that PET films (polyethylene terephthalate films of EMBLET (trade mark) S-75 (trade name) by Unitika Ltd.) were employed in place of the FEP films, and subjected to evaluation similarly to Example 1. Table 2 shows the results.

TABLE 2

Amount of Leukocytes Adsorbed PET Film

| | Film | | | | | |
|---|---|---|---|---|---|---|
| | Comparative Example | | | Example | | |
| | 4 | 5 | 6 | 4 | 5 | 6 |
| | | | Polished | | | Polished |
| Item | Un-polished | 4000 meshes | 2400 | 1200 | 500 meshes | 220 |
| Ra Value (μm) | 0.10 | 0.08 | 0.19 | 0.61 | 1.55 | 2.24 |
| Sm Value (μm) | 475 | 36.7 | 125.7 | 30.6 | 46.6 | 76.5 |
| Amount of Adsorbed Leukocytes (pieces/mm$^2$) | 104 | 90 | 105 | 1151 | 805 | 963 |
| Relative Adsorption Ratio | 1 | 0.87 | 1.01 | 11.1 | 7.74 | 9.26 |

As clearly understood from Table 2, the amounts of adsorbed leukocytes were abruptly increased when the value Ra exceeded 0.61 μm. For example, the film according to Example 4 having surface roughness Ra of 0.61 μm, which was obtained by polishing with sand paper of 1200 meshes, exhibited an amount of adsorbed leukocytes of 11.1 times as compared with that of the unpolished film (comparative example 4), while the polished films of Examples 5 and 6 having Ra values of 1.55 μm and 2.24 μm respectively exhibited amounts of adsorbed leukocytes of 7.74 times and 9.26 times as compared with that of the unpolished film (comparative example 4) respectively.

On the other hand, Sm values of the polished films were within a range of 30 to 130 μm, while that of the unpolished film according to comparative example 4 was 475 μm.

Examples 7 to 9 and Comparative Examples 7 to 9

Unpolished and polished films were prepared similarly to Examples 1 to 3 and comparative examples 1 to 3, except that CA films (cellulose acetate films of ACETYLOID VR-R (trade name) by ARTPLUS CORPORATION) were employed in place of the FEP films, subjected to Soxhlet extraction with methyl alcohol for 24 hours in place of washing with methyl alcohol for extracting plasticizers, and the films were then taken out, air-dried for 15 hours and further dried at 80° C. for 5 hours, to be subjected to evaluation similarly to Example 1. Table 3 shows the results.

TABLE 3

Amount of Leukocytes Adsorbed CA Film

| | Film | | | | | |
|---|---|---|---|---|---|---|
| | Comparative Example | | | Example | | |
| | 7 | 8 | 9 | 7 | 8 | 9 |
| | | | Polished | | | Polished |
| Item | Un-polished | 4000 meshes | 2400 meshes | 1200 meshes | 500 meshes | 220 meshes |
| Ra Value (μm) | 0.05 | 0.05 | 0.06 | 0.58 | 1.28 | 2.37 |
| Sm Value (μm) | 250 | 125 | 31 | 30 | 44 | 57 |
| Amount of Adsorbed Leukocytes (pieces/mm$^2$) | 131 | 170 | 200 | 514 | 309 | 343 |
| Relative Adsorption Ratio | 1 | 0.87 | 1.30 | 3.92 | 2.36 | 2.62 |

As clearly understood from Table 3, the amounts of absorbed leukocytes were abruptly increased in the polished films having Ra values of at least 0.58 μm, which were polished with sand paper of not more than 1200 meshes. For example, the polished films of Examples 7, 8 and 9 having Ra values of 0.58 μm, 1.28 μm and 2.37 μm respectively exhibited amounts of adsorbed leukocytes of 3.92 times, 2.36 times and 2.62 times as compared with that of the unpolished film (comparative example 7).

Examples 10 to 12 and Comparative Examples 10 to 12

Five types of polished films were prepared with surface roughness values Ra of at least 0.6 μm and Sm values in a range of 30 to 370 μm similarly to Examples 4 to 6, except that the films were polished with sand paper of 1200 meshes with various polishing times (see Table 4). The five types of polished films and an unpolished PET film (comparative example 10) were prepared to be subjected to a leukocyte film adsorption test, similarly to Example 1. Table 4 shows the results.

TABLE 4

Sa Value of and Amount of Leukocytos Adsorbed by Polished PEP Film

| | Film | | | | | |
|---|---|---|---|---|---|---|
| | Comparative Example | | | Example | | |
| | 10 | 11 | 12 | 10 | 11 | 12 |
| Item | Un-polished | Polished | Polished | | Polished | Polished |
| Sm value (μm) | 10 | 374 | 213 | 101 | 56 | 31 |
| Ra Value (μm) | 0.10 | 0.81 | 0.87 | 0.69 | 0.75 | 0.78 |
| Amount of Adsorbed Leukocytes (pieces/mm$^2$) | 91 | 90 | 105 | 876 | 805 | 751 |
| Relative Adsorption Ratio | 1 | 0.99 | 1.17 | 9.63 | 8.85 | 8.25 |

It is clearly understood from Table 4 that the films of Examples 10 to 12 having Sm values of not more than 200 μm exhibited extremely large amounts of adsorbed leukocytes, as compared with the films of comparative examples 10 to 12 having Sm values exceeding 200 μm. While the polished films of comparative examples 11 and 12 having Sm values exceeding 200 μm exhibited amounts of adsorbed leukocytes which were substantially similar to that of the unpolished PET film (comparative example 10), the polished films of Examples 10 to 12 exhibited amounts of adsorbed leukocytes of at least eight times as compared with that of the unpolished PET film (comparative example 10).

While excellent leukocyte adsorbability was confirmed in relation to Examples 1 to 12, it can be inferred that the polished films of Examples 1 to 12 similarly exhibit remarkable effects as compared with those of comparative examples also in granulocyte adsorbability, since the leukocyte adsorbability has correlation with granulocyte adsorbability as hereinabove described.

Example 13 and Comparative Example 13

Nylon 66 pellets (UBE66 2020B (trade name) by Ube Industries, Ltd.) were injection-molded to prepare spherical beads of 2.5 mm in diameter. These beads exhibited Ra and Sm values of 0.21 μm and 294 μm respectively.

Polished beads were prepared by introducing 200 ml of the aforementioned beads and the same amount of an abrasive (WHITE ABRAX (WA) #34 (trade name) by JAPAN ABRASIVE CO., LTD.) into a pot mill (51-Ceramic Pot Mill Bp-5 (trade name) by Toyobo Engineering Co., Ltd.) while further introducing several balls for a ceramic pot mill (BB-13 (trade name) by Toyobo Engineering Co., Ltd.) and polishing the beads with a ball polishing machine (pot mill AN-3S (trade name) by NITTO KAGAKU CO., LTD.) for five hours. Thus, polished beads having Ra and Sm values of 9.1 μm and 124 μm respectively were obtained and 3 g of these polished beads and 3 g of unpolished beads were employed as adsorbing carriers to be subjected to the aforementioned bead adsorption experiment. Table 5 shows the results.

TABLE 5

Amount of Leukocytes Adsorbed by Nylon Beads

| | Item | | | |
|---|---|---|---|---|
| | Center Line | Mean Spacing | Amount of Adsorption (pieces/g) | |
| Type of Beads | Average Height (μm) | Sm of Unevenness (μm) | Number of Granulocytes | Number of Lymphocytes |
| Comparative Example 13 (Unpolished Beads) | 0.210 | 294.4 | $2.6 \times 10^5$ | $1.5 \times 10^4$ |
| Example 13 (Polished Beads) | 9.1 | 123.5 | $1.2 \times 10^6$ | $1.8 \times 10^4$ |

As clearly understood from Table 5, the polished beads (Example 13) exhibited granulocyte adsorbability of 4.6 times that of the unpolished beads (comparative example 13), while the amount of adsorbed lymphocytes of the former was substantially similar to that of the latter.

Example 14 and Comparative Example 14

A cellulose acetate pellet (by ARTPLUS CORPORATION, containing 30 percent by weight of acetyltriethyl citrate as a plasticizer) was injection-molded to prepare beads of 2.3 mm in diameter. 50 g of these beads were subjected to Soxhlet extraction with 300 ml of methanol at 50° C. for 24 hours, to extract the plasticizer. Thereafter the beads from which the plasticizer was extracted were taken out in a vat of stainless steel, air-dried for 15 hours, and thereafter further dried at 80° C. for 5 hours, to obtain beads having an Ra value of 0.186 μm and an Sm value of 298.7 μm. Then, the beads were molded and polished similarly to Example 13, to obtain polished beads (Example 14) having an Ra value of 1.36 μm and an Sm value of 97.2 μm, which were subjected to the aforementioned bead adsorption experiment with unpolished beads (comparative example 14). Table 6 shows the results.

TABLE 6

Amount of Leukocytes Adsorbed by CA Beads

| | Item | | | |
|---|---|---|---|---|
| | Center Line | Mean Spacing | Amount of Adsorption (pieces/g) | |
| Type of Beads | Average Height (μm) | Sm of Uneveness (μm) | Number of Granulocytes | Number of Lymphocytes |
| Comparative Example 14 (Unpolished Beads) | 0.186 | 298.7 | $1.3 \times 10^5$ | $1.9 \times 10^4$ |
| Example 14 (Polished Beads) | 1.36 | 97.2 | $1.5 \times 10^6$ | $2.2 \times 10^4$ |

As understood from Table 6, the polished beads (Example 14) exhibited granulocyte adsorbability of 11.5 times that of the unpolished beads (comparative example 14), while no difference was recognized in lymphocyte adsorbability.

Example 15 and Comparative Example 15

CA beads (unpolished) obtained in comparative example 14 were dipped in a solution of methylene chloride-ethanol (weight ratio: 9:1) containing 1 percent by weight of cellulose acetate (Cellulose Acetate by Daicel Chemical Industries, Ltd.) in which 2 percent by weight of particulates (by Sekisui Chemical Co., Ltd., 3 μm in diameter) of a styrene-divinyl benzene copolymer (copolymerization ratio: 1:1) prepared by suspension polymerization were suspended, and thereafter air-dried to prepare particulate-coated beads (Example 15).

It was confirmed with an electron microscope that the surfaces of the beads were coated with the aforementioned particulates by cellulose acetate.

3 g of the particulate-coated beads (Example 15) obtained in the aforementioned manner and 3 g of uncoated beads (comparative example 15) were subjected to the aforementioned bead adsorption test. Table 7 shows the results.

TABLE 7

Amount of Leukocytes Adsorbed by Particulate-Coated CA Beads

| | Item | | | |
|---|---|---|---|---|
| | Center Line | Mean Spacing | Amount of Adsorption (pieces/g) | |
| Type of Beads | Average Height (μm) | Sm of Uneveness (μm) | Number of Granulocytes | Number of Lymphocytes |
| Comparative Example 15 (Uncoated Beads) | 0.167 | 201.7 | $2.2 \times 10^5$ | $3.1 \times 10^4$ |
| Example 15 (Coated Beads) | 2.46 | 62.5 | $3.1 \times 10^6$ | $4.4 \times 10^4$ |

As clearly understood from Table 7, the particulate-coated beads (Example 15), having an Ra value of 2.46 μm and an Sm value of 62.5 μm, exhibited granulocyte adsorbability which was 14.1 times that of the uncoated beads (comparative example 15), while lymphocyte adsorbability of the former was substantially similar to that of the latter.

Example 16 Comparative Example 16

A nylon 66 pellet (by Ube Industries, Ltd.) was injection-molded as a porous carrier to be employed for a granulocyte adsorption experiment, to prepare beads of 2.3 mm in particle diameter. A solution of methylene chloride/ethanol (weight ratio: 9:1) containing 5 percent by weight of cellulose acetate resin (by Daicel Chemical Industries, Ltd.) for serving as a coating solution was sprayed onto 4.6 kg of the beads with a flow coater (FLO-5 (trade name) by FREUND IND. CO., LTD), to prepare beads which were coated with cellulose acetate resin. The coated beads were subjected to observation through phototaking with a scanning electron microscope. As the result, it was confirmed that surface-porous beads having coating layers of 200 μm were obtained. Coating conditions were as follows:

Spray Air Pressure: 3.5 kg/cm$^2$
Spray Solution Temperature: Room Temperature
Spray Solution Flow Rate: 100 ml/min.
Spray Temperature: 60° C.
Spray Nozzle Diameter: 1:2 mm 3 g of the coated beads (Example 16) obtained in the aforementioned manner and 3 g of uncoated beads (comparative example 16) were subjected to the aforementioned bead adsorption test. Table 8 shows the results.

TABLE 8

Amount of Leukocytes Adsorbed by Surface-Porous Beads

| | Item | | | |
|---|---|---|---|---|
| | Center Line | Mean Spacing | Amount of Adsorption (pieces/g) | |
| Type of Beads | Average Height (μm) | Sm of Uneveness (μm) | Number of Granulocytes | Number of Lymphocytes |
| Comparative Example 16 (Non-Porous Beads) | 0.210 | 294.4 | $2.6 \times 10^5$ | $1.5 \times 10^4$ |

TABLE 8-continued

Amount of Leukocytes Adsorbed by Surface-Porous Beads

| | Item | | | |
|---|---|---|---|---|
| | Center Line | Mean Spacing | Amount of Adsorption (pieces/g) | |
| Type of Beads | Average Height (μm) | Sm of Uneveness (μm) | Number of Granulocytes | Number of Lymphocytes |
| Example 16 (Porous Beads) | 1.18 | 5.8 | $1.9 \times 10^6$ | $2.1 \times 10^4$ |

As clearly understood from Table 8, the coated beads (Example 16), having an Ra value of 1.18 μm and an Sm value of 5.8 μm, exhibited granulocyte adsorbability of 7.3 times that of the uncoated beads (comparative example 16), while lymphocyte adsorbability of the former was substantially similar to that of the latter.

Example 17 and Comparative Example 17

A column which was prepared by fixing a polyester net (T-No. 70s (trade name) by NBC INDUSTRIES CO., LTD.) to a polycarbonate column of 29 mm in inner diameter and 90 mm in length and sealing the same with a polypropylene net was filled up with the CA beads of Example 14 and a 0.9 wt. % sodium chloride aqueous solution and sterilized in an autoclave at 120° C. for 20 minutes, to prepare a column (hereinafter referred to as this column) for rabbit extracorporeal circulation.

Figure 6:
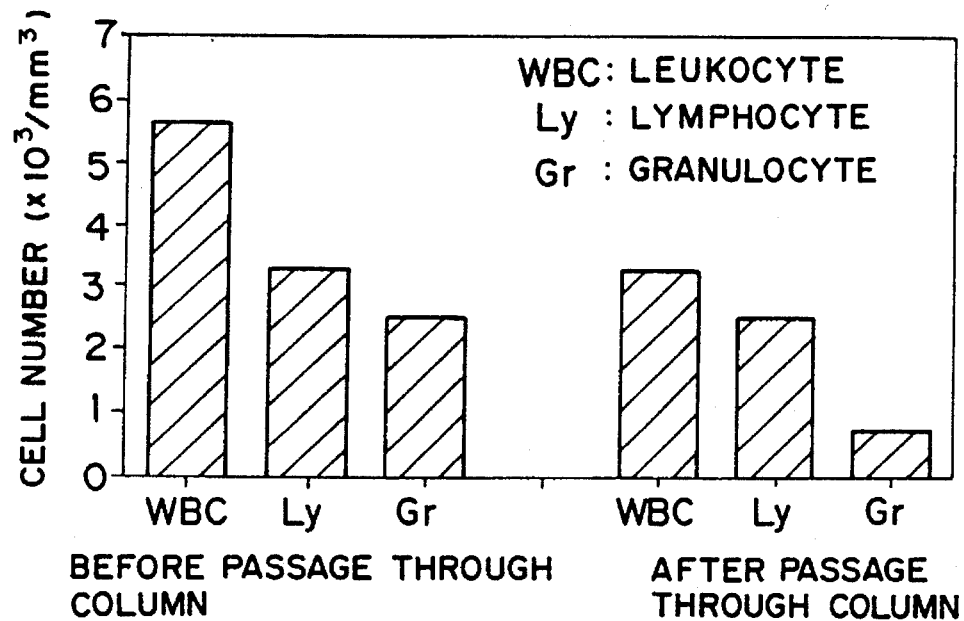
FIG. 6 illustrates concentration changes of leukocytes in blood in rabbit extracorporeal circulation measured in an experiment of Example 17.

An efficacy test for this column was made on six Japanese white rabbits (female) of 3 kg in weight. An alar acus was inserted in an ear vein of each rabbit to guide the blood to this column and reflux the same to the opposite ear vein through a peristaltic pump at a flow rate of 1 ml/min. Immediately after starting of the reflux, concentration values of granulocytes and lymphocytes in the blood before and after flowing of the blood into the column by an H-1 hemocytometer by Technicon Instruments Corporation. FIG. 6 shows the results. As the result, the number of the granulocytes contained in the blood, which was $2406/mm^3$ in an inlet of the column, was reduced to about ¼ of $588/mm^3$ in an outlet of the column. On the other hand, reduction of the number of the lymphocytes remained at about 20% from $3218/mm^3$ to $2501/mm^3$.

Further, $1 \times 10^7$ tumor cells ($VX_2$) resulting from Shobe papilloma were subcutaneously implanted into the back of each rabbit (n=6) of the same type as the above and extracorporeal circulation was carried out when the tumor area reached 400 to 500 $mm^2$, to be repeated in a cycle of a reflux time of 2 hours and a flow rate of 1 ml/min. This extracorporeal circulation was carried out twice a week up to the fourth week after starting of this experiment, and thereafter carried out once a week up to the tenth week. Then, tumor resistance was studied. Rabbits (n=4) which were not treated with this column after implantation of tumors were employed as controls and progresses thereof were observed. Antitumor effects were judged from transition of tumor areas (longer diameter/2×shorter diameter/2× $\pi(mm^2)$).

Figure 7:
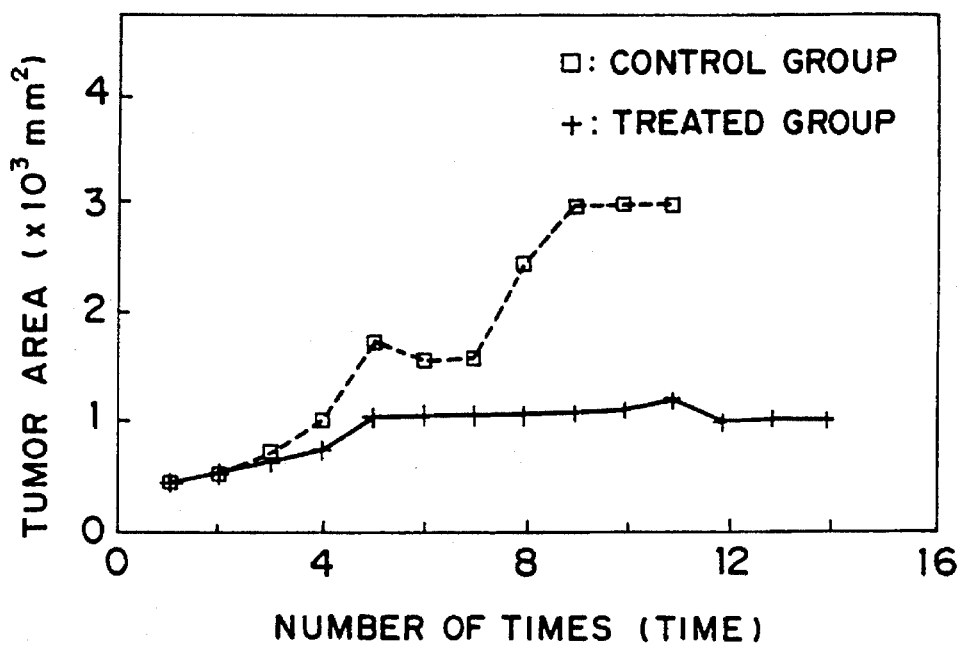
FIG. 7 illustrates changes over time in tumor areas measured in Example 17.

As shown in FIG. 7, effects of suppressing tumor enhancement were clearly observed in the rabbits treated with this column, while the tumor areas were gradually increased after implantation of the tumors in the controls.

B. Examples of the Invention on Method of Preparing Granulocyte Adsorbing Carrier Experiment of ATEC Extraction with Various Extraction Solvents A cellulose acetate pellet (ACETYLOID (trade name) by ARTPLUS CORPORATION, containing 30 percent of ATEC) was injection-molded to prepare beads of 2.3 in particle diameter. ATEC was extracted from about 200 mg of the beads as obtained, with 5 ml of methanol, ethanol, isopropyl alcohol, n-hexane and diethyl ether repectively at the room temperature for 24 hours. Rates of extraction were calculated from ATEC concentration values in the respective solvents after extraction. Table 9 shows the results.

TABLE 9

Rate of Extraction from Beads

| Solvent | Rate of Extraction (%) |
|---|---|
| Methanol | 68 |
| Ethanol | 38 |
| Isopropyl Alcohol | 12 |
| n-Hexane | 1 |
| Diethyl Ether | 23 |

As clearly understood from Table 9, methanol and ethanol having strong polarity exhibited high rates of extraction. However, ethanol also influenced on the cellulose acetate resin. In fact, the beads were whitened after extraction and a particulate generation test employing the beads was unsuitable to an insoluble particulate test of "injection" under General Rules for Preparations, the Pharmacopeia of Japan, 11th Edition. While isopropyl alcohol, n-hexane and diethyl ether having relatively high hydrophobicity exert no influence on cellulose acetate resin, these solvents have inferior extraction efficiency as understood from Table 9.

ATEC Toxicity Test

A prescribed amount of ATEC (supplied by Pfizer Pharmaceutical Inc.) was added to a 0.25 wt. % Tween 80-physiological physiological saline to prepare a test solution so that the ATEC dose was 10 ml/kg. Various doses of such test solutions were administered into caudal veins of male ddy mice of 6 weeks, to find that the lethal dosage was 400 mg/kg.

For the purpose of comparison, a prescribed amount of dioctyl phthalate (by Kanto Chemical Co., Ltd.) was added to a 0.25 wt. % Tween 80-physiological saline to prepare a test solution so that the ATEC dose was 10 ml/kg. Various doses of such test solutions were administered into caudal veins of male ddy mice of 6 weeks, to find that the lethal dosage was 160 mg/kg.

Example 21

A cellulose acetate pellet (ACETYLOID by ARTPLUS COPRORATION, containing 30 percent by weight of ATEC) was injection-molded to prepare beads of 2.3 mm in particle diameter. About 200 g of the beads as obtained were introduced into a glass reactor of 5 liters provided with a condenser, and subjected to extraction with 3 liters of methanol at 50° C. for 1 hour. After the extraction, the methanol was removed by decantation. This extraction was repeated five times in total, and thereafter the beads were taken out in a vat of stainless steel, air-dried for 15 hours and thereafter further dried at 80° C. for 5 hours, to prepare a granulocyte adsorbing carrier.

200 g of the granulocyte adsorbing carrier as obtained was dissolved in 5 ml of a solution containing dichloromethane and methanol in a volume ratio of 9:1, diluted with methanol to 10 times, and subjected to centrifugation at 20000 rpm for 20 minutes. Thereafter the supernatant was taken, filtered and measured by a gas chromatograph (GC-15A (trade name) by Shimadzu Corporation) with a column (G-column (G-250) (trade name) by Chemicals Inspection & Testing Institute. JAPAN) at a column temperature of 170° C. The plasticizer content was 0.5 percent by weight.

1.5 g of the aforementioned granulocyte adsorbing carrier was subjected to an eluate test under the dialysis type artificial kidney approval standards. The effluent as obtained was introduced into a rectangular quartz cell of 10 mm in layer length, and subjected to measurement of adsorbance at wavelengths of 220 to 350 nm (with a spectrophotometer by Shimadzu Corporation). It was confirmed that this carrier, exhibiting the maximum adsorbance of 0.03, is conformable to the aforementioned standard.

Comparative Example 21

A cellulose acetate pellet (ACETYLOID (trade name) by ARTPLUS CORPORATION, containing 30 percent by weight of diethyl phthalate) was injection-molded to prepare beads of 2.3 mm in particle diameter. About 200 g of the beads as obtained were introduced into a glass reactor of 5 liters provided with a condenser and subjected to extraction with 3 liters of methanol at 50° C. for 1 hour. After the extraction, the methanol was removed by decantation. This extraction was repeated five times in total, and thereafter the beads were taken out in a vat of stainless steel, air-dried for 15 hours and thereafter further dried at 80° C. for 5 hours, to prepare a granulocyte adsorbing carrier. 200 g of the granulocyte adsorbing carrier as obtained was dissolved in 5 ml of a solution containing dichloromethane and methanol in a volume ratio of 9:1, diluted with methanol to 10 times, and subjected to centrifugation at 20000 rpm for 20 minutes. Thereafter the supernatant was taken and filtered, and the content of diethyl phthalate serving as a plasticizer was measured similarly to Example 21. The plasticizer content was 0.5 percent by weight.

1.5 g of the aforementioned granulocyte adsorbing carrier was subjected to an eluate test under the dialysis type artificial kidney approval standards, similarly to Example 21. As the result, this carrier exhibited the maximum adsorbance of 1.02, which was higher than the reference value of 0.1.

Example 22

50 g of beads which were prepared similarly to Example 21 were filled up in a column which was prepared by fixing a polyester net (T-No. 70s (trade name) by NBC INDUSTRIES CO., LTD.) to a polycarbonate column of 29 mm in inner diameter and 90 mm in length and sealing the same with a polypropylene net, and washed with 200 ml of a physiological salt solution (by Otsuka Pharmaceutical Co., Ltd.) which was fed at a flow rate of 16 ml/sec. After the washing, air was fed to discharge the physiological salt solution from the column, human blood plasma (Seracon II by the Center for Diagnostic Products) was filled up in the column from its lower end. The human blood plasma was circulated under the room temperature at a flow rate of 15 ml/sec. for 6 hours.

After the circulation, 30 ml of the blood plasma was stirred with addition of 30 ml of acetone, and subjected to centrifugation at 3200 rpm for 15 minutes, to collect the supernatant. This supernatant was further stirred with addition of 30 ml of acetone, subjected to centrifugation at 3200 rpm for 15 minutes, and collected. This supernatant was dried/solidified, and dissolved in 5 ml of acetone. The amount of ATEC contained in the solution as obtained was measured by gas chromatography, similarly to Example 21.

The ATEC content as measured was 0.65 mg in terms of elution per 228 g of the beads employed for human extracorporeal circulation.

Comparative Example 22

1000 ml of a physiological salt solution (by Otsuka Pharmaceutical Co., Ltd.) was fed into a set of a blood circuit for an artificial kidney (clearance blood circuit BH by Terumo Corporation) at a flow rate of 50 ml, to wash the same. After the washing, air was fed to discharge the physiological salt solution, and human blood plasma (Seracon II by the Center for Diagnostic Products) was filled up in the circuit. Circulation was made under the room temperature at a flow rate of 15 ml/sec. for 6 hours. After the circulation, 30 ml of the blood plasma was stirred with addition of 30 ml of acetone, and subjected to centrifugation at 3200 rpm for 15 minutes, to collect the supernatant. This supernatant was further stirred with addition of 30 ml of acetone, subjected to centrifugation at 3200 rpm for 15 minutes, and collected. The amount of dioctyl phthalate contained in the collected supernatant was measured by gas chromatography similarly to Example 22, except that the column temperature was set at 230° C.

The amount of elution of the dioctyl phthalate from the artificial kidney blood circuit was 37.5 mg. As compared with the amount of 0.65 mg in Example 22 in terms of an amount per that of the beads employed for human extracorporeal circulation, the amount of elution in Example 22 was about 1/57 of that in the artificial kidney blood circuit of comparative example 22.

Example 23

2 g of the granulocyte adsorbing carrier prepared in Example 21 was filled up in a 5 ml disposer pull syringe (by Terumo Corporation), and incubated at 37° C. for 60 minutes with addition of 2 ml of fresh human blood containing 5 U/ml of heparin. During the incubation, soft inversion mixing was made every 5 to 10 minutes. After the incubation, the blood was collected by natural dropping, to prepare a smear sample. This sample was dipped in a 50% May-Gr ünwald solution (phosphoric acid buffer solution of pH 6.4) for 15 minutes, stained with a 3% Giemsa solution for 30 minutes and subjected to leukocyte classification under a microscope, to obtain the results shown in Table 10.

TABLE 10

| | Change of G-L Ratio by Adsorption Experiment | | | |
| --- | --- | --- | --- | --- |
| | Leukocyte Classification (%) | | | |
| Sample | Granulocyte | Lymphocyte | Monocyte | G/L |
| Unadsorbed Blood | 64.2 | 33.5 | 2.3 | 1.91 |
| Adsorbed Blood | 29.5 | 68.6 | 1.9 | 0.43 |

Example 24

Figure 8:
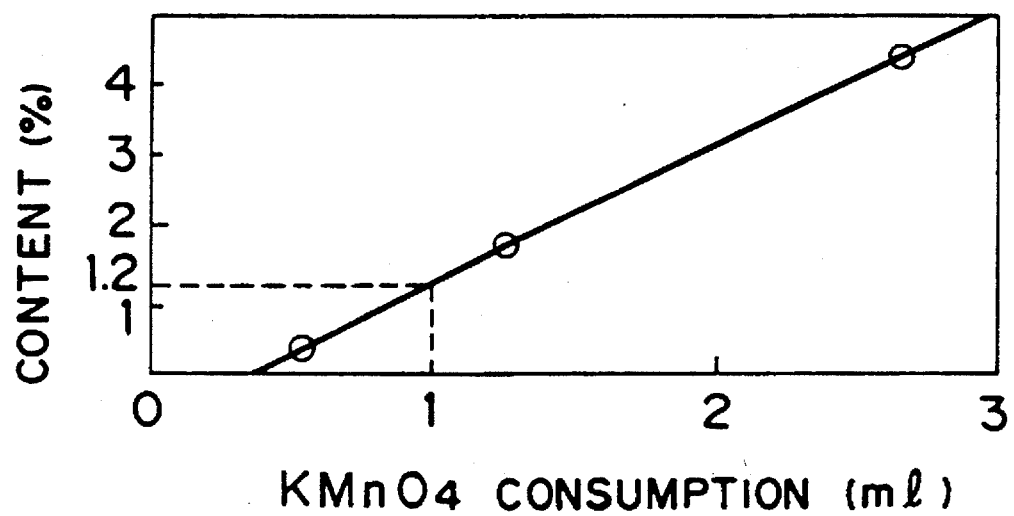
FIG. 8 illustrates relations between plasticizer contents and amounts of $KMnO_4$ consumption.

Extraction and measurement of a plasticizer content which were similar to those in Example 21 were carried out on a material which was similar to that in Example 21, and methanol was batch-extracted three, four and five times to obtain beads having residual ATEC contents of 4.3, 1.7 and 0.5 percent by weight respectively. The respective bead samples as obtained were subjected to a potassium permanganate consumption test of a water eluate test under the Notification of Director-general of Pharmaceutical affairs bureau M.H.W. No. 494 dialysis type artificial kidney device approval standards. FIG. 8 shows the results. As understood from FIG. 8, it was recognized that a reference value of potassium permanganate consumption of not more than 1 ml corresponds to a plasticizer content of not more than 1.2%.

As hereinabove described, the granulocyte adsorbing carrier according to the present invention which is provided on its surface with irregularities of the aforementioned specific ranges can adsorb granulocytes in high efficiency.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A granulocyte remover comprising:
   a granulocyte adsorbing part storing a granulocyte adsorbing carrier being provided on its surface with irregularities having a center line average height Ra, being defined under Japanese Industrial Standard B0601-1982, of 0.2 μm to 10 μm and a mean spacing Sm of unevenness being within a range of 5 μm to 200 μm;
   a blood incurrent part for introducing blood into said granulocyte adsorbing part; and
   blood excurrent part for discharging said blood being introduced into said granulocyte adsorbing part to the exterior thereof.

2. A granulocyte remover in accordance with claim 1, wherein said granulocyte adsorbing part is formed by a cylindrical column.

3. A granulocyte remover in accordance with claim 2, wherein said granulocyte adsorbing carrier being filled up in said column is a granulocyte adsorbing carrier in the form of beads.

* * * * *